(12) United States Patent
Bush et al.

(10) Patent No.: US 10,005,978 B2
(45) Date of Patent: Jun. 26, 2018

(54) DIESEL DETERGENT WITHOUT A LOW MOLECULAR WEIGHT PENALTY

(71) Applicant: The Lubrizol Corporation, Wickliffe, OH (US)

(72) Inventors: James H. Bush, Mentor, OH (US); Robert H. Barbour, Ashborne (GB); David J. Moreton, Belper (GB); Hannah Greenfield, Derby (GB); Paul R. Stevenson, Belper (GB); David C. Arters, Solon, OH (US)

(73) Assignee: The Lubrizol Corporation, Wickliffe, OH (US)

( * ) Notice: Subject to any disclaimer, the term of this patent is extended or adjusted under 35 U.S.C. 154(b) by 26 days.

(21) Appl. No.: 14/434,965

(22) PCT Filed: Oct. 22, 2013

(86) PCT No.: PCT/US2013/066110
§ 371 (c)(1),
(2) Date: Apr. 10, 2015

(87) PCT Pub. No.: WO2014/066344
PCT Pub. Date: May 1, 2014

(65) Prior Publication Data
US 2015/0267138 A1  Sep. 24, 2015

Related U.S. Application Data

(60) Provisional application No. 61/717,161, filed on Oct. 23, 2012.

(51) Int. Cl.

| | |
|---|---|
| C10L 10/04 | (2006.01) |
| C10L 1/22 | (2006.01) |
| C07C 235/10 | (2006.01) |
| C10L 1/08 | (2006.01) |
| C07D 207/408 | (2006.01) |
| C07D 303/04 | (2006.01) |
| C08G 63/91 | (2006.01) |
| C10L 1/222 | (2006.01) |
| C10L 1/224 | (2006.01) |
| C10L 1/238 | (2006.01) |
| C10L 1/2383 | (2006.01) |
| C10L 1/2387 | (2006.01) |
| C10L 10/06 | (2006.01) |
| C10L 10/18 | (2006.01) |
| C10L 10/02 | (2006.01) |
| C10L 1/232 | (2006.01) |

(52) U.S. Cl.
CPC ............ *C10L 10/04* (2013.01); *C07C 235/10* (2013.01); *C07D 207/408* (2013.01); *C07D 303/04* (2013.01); *C08G 63/912* (2013.01); *C10L 1/08* (2013.01); *C10L 1/22* (2013.01); *C10L 1/221* (2013.01); *C10L 1/224* (2013.01); *C10L 1/2222* (2013.01); *C10L 1/2225* (2013.01); *C10L 1/238* (2013.01); *C10L 1/2383* (2013.01); *C10L 1/2387* (2013.01); *C10L 10/06* (2013.01); *C10L 10/18* (2013.01); *C10L 1/232* (2013.01); *C10L 10/02* (2013.01); *C10L 2200/0259* (2013.01); *C10L 2230/22* (2013.01); *C10L 2270/026* (2013.01)

(58) Field of Classification Search
USPC .................... 123/1 A; 44/347, 353; 548/546; 549/512
See application file for complete search history.

(56) References Cited

U.S. PATENT DOCUMENTS

| | | | |
|---|---|---|---|
| 4,056,531 A | 11/1977 | Malec | |
| 4,171,959 A | 10/1979 | Vartanian | |
| 5,254,138 A * | 10/1993 | Kurek | C08F 8/44 44/338 |
| 2008/0207826 A1* | 8/2008 | Thetford | B01F 17/0028 524/556 |

FOREIGN PATENT DOCUMENTS

| | | |
|---|---|---|
| CA | 2804322 A1 | 1/2012 |
| WO | 88/09365 A1 | 12/1988 |
| WO | 99/11693 A1 | 3/1999 |
| WO | 2010/097624 A1 | 9/2010 |
| WO | 2011/095819 A1 | 8/2011 |
| WO | 2011/110860 A1 | 9/2011 |
| WO | 2012/004300 A1 | 1/2012 |
| WO | 2012/071313 A1 | 5/2012 |

* cited by examiner

*Primary Examiner* — Ellen McAvoy
*Assistant Examiner* — Chantel Graham
(74) *Attorney, Agent, or Firm* — Iken S. Sans; Christopher P. Demas

(57) ABSTRACT

The composition of the present invention related to a quaternary ammonium salt detergent and the use of such quaternary ammonium salt detergents in a fuel composition to reduce diesel injector deposits and remove or clean up existing deposits on the diesel injectors.

11 Claims, No Drawings

DIESEL DETERGENT WITHOUT A LOW MOLECULAR WEIGHT PENALTY

CROSS REFERENCE TO RELATED APPLICATION

This application claims priority from PCT Application Ser. No. PCT/US2013/066110 filed on Oct. 22, 2013, which claims the benefit of U.S. Provisional Application No. 61/717,161 filed on Oct. 23, 2012.

BACKGROUND OF THE INVENTION

The composition of the present invention is related to a quaternary ammonium salt detergent and the use of such quaternary ammonium salt detergents in a fuel composition to reduce diesel injector deposits and remove or clean up existing deposits on the diesel injectors.

It is well known that liquid fuel contains components that can degrade during engine operation and form deposits. These deposits can lead to incomplete combustion of the fuel resulting in higher emission and poorer fuel economy. Fuel additives, such as detergents, are well known additives in liquid fuels to help with control or minimize deposit formation. As the dynamics and mechanics of an engine continual advance, the requirements of the fuel must evolve to keep up with these engine advancements. For example, today's engines have injector system that have smaller tolerances and operate at higher pressure to enhance fuel spray to the compression or combustion chamber. Deposit prevention and deposit reduction in these new engines has become critical to optimal operation of today's engines. Advancements in fuel additive technology, such as detergents, have enabled the fuel to keep up with these engine advancements. Therefore there is a need for detergent capable of providing acceptable performance in a liquid fuel to promote optimal operation of today's engines.

U.S. Pat. No. 5,000,792 discloses polyesteramine detergent obtainable by reacting 2 parts of polyhydroxycarboxylic acids with 1 part of dialkylenetriamine.

U.S. Pat. No. 4,171,959 discloses a motor fuel composition containing quaternary ammonium salts of a succinimide. The quaternary ammonium salt has a counterion of a halide, a sulphonate or a carboxylate.

U.S. Pat. Nos. 4,338,206 and 4,326,973 discloses fuel compositions containing a quaternary ammonium salt of a succinimide, wherein the ammonium ion is heterocyclic aromatic (pyridinium ion).

U.S. Pat. No. 4,108,858 discloses a fuel or lubricating oil composition containing a C2 to C4 polyolefin with a Mw of 800 to 1400 salted with a pyridinium salt.

U.S. Pat. No. 5,254,138 discloses a fuel composition containing a reaction product of a polyalkyl succinic anhydride with a polyamino hydroxyalkyl quaternary ammonium salt.

U.S. Pat. No. 4,056,531 discloses a lubricating oil or fuel containing a quaternary ammonium salt of a hydrocarbon with a Mw of 350 to 3000 bonded to triethylenediamine. The quaternary ammonium salt counterion is selected from halides, phosphates, alkylphosphates, dialkylphosphates, borates, alkylborates, nitrites, nitrates, carbonates, bicarbonates, alkanoates, and O,O-dialkyldihtiophosphates.

U.S. Pat. No. 4,248,719 discloses a fuel or lubricating oil containing a quaternary ammonium salt of a succinimide with a monocarboxylic acid ester. U.S. Pat. No. 4,248,719 does not teach, suggest or otherwise disclose low sulphur fuels, presence of fluidisers etc. Example 1 teaches poly- isobutylene succinimide with DMAPA as the amine. The succinimide is then reacted with a salicylate.

U.S. Pat. Nos. 4,253,980 and 4,306,070 disclose a fuel composition containing a quaternary ammonium salt of an ester-lactone.

U.S. Pat. No. 3,778,371 discloses a lubricating oil or fuel containing a quaternary ammonium salt of a hydrocarbon with a Mw of 350 to 3000; and the remaining groups to the quaternary nitrogen are selected from the group of C1 to C20 alkyl, C2 to C8 hydroxyalkyl, C2 to C20 alkenyl or cyclic groups.

US 2011/0302828 to Fang et al., published Dec. 15, 2011 discloses a diesel fuel composition containing diesel fuel additive having a number average molecular weight of 500 to 10,000, wherein less than 25 wt % of the additive has a molecular weight of 400 or less.

The present invention, therefore, promotes optimal engine operation, that is, increased fuel economy, better vehicle drivability, reduced emissions and less engine maintenance by reducing, minimizing and controlling deposit formation.

SUMMARY OF THE INVENTION

The present invention further provides a method for fueling an internal combustion engine, comprising:
A. supplying to said engine:
   I. a fuel which is liquid at room temperature; and
   II. quaternary ammonium salt comprising the reaction product of:
      (a) a compound comprising (i) at least one tertiary amino group, and (ii) a hydrocarbyl-substituent having a number average molecular weight of from about 100 to about 500; and
      (b) a quaternizing agent suitable for converting the tertiary amino group of (a)(i) to a quaternary nitrogen,
   wherein the quaternizing agent is selected from the group consisting of dialkyl sulfates, benzyl halides, hydrocarbyl substituted carbonates; hydrocarbyl epoxides, hydrocarbyl epoxides in combination with an acid, or mixtures thereof.

The present invention additionally provides for a composition comprising a quaternary ammonium salt, wherein the quaternary ammonium salt comprises the reaction product of:
(a) a compound comprising (i) at least one tertiary amino group, and
(ii) a hydrocarbyl-substituent having a number average molecular weight of from about 100 to about 500; and
(b) a quaternizing agent suitable for converting the tertiary amino group of (a)(i) to a quaternary nitrogen.

The above compositions can additionally comprise a quaternary ammonium salt, wherein the quaternary ammonium salt comprises the reaction product of:
(a) a compound comprising (i) at least one tertiary amino group, and
(ii) a hydrocarbyl-substituent derived from a hydrocarbon having a number average molecular weight of from about 500 to about 5000; and
(b) a quaternizing agent suitable for converting the tertiary amino group of compound (a) to a quaternary nitrogen

DETAILED DESCRIPTION OF THE INVENTION

Various preferred features and embodiments will be described below by way of non-limiting illustration.

This invention involves a quaternary ammonium salt, a fuel composition that includes the quaternary ammonium salt, and a method of operating an internal combustion engine with the fuel composition. The compositions and methods of the present invention minimize, reduce and control deposit formation in the engine, which reduces fuel consumption, promotes drivability, vehicle maintenance, and reduces emissions which enables optimal engine operation.

Fuel

The composition of the present invention can comprise a fuel which is liquid at room temperature and is useful in fueling an engine. The fuel is normally a liquid at ambient conditions e.g., room temperature (20 to 30° C.). The fuel can be a hydrocarbon fuel, a nonhydrocarbon fuel, or a mixture thereof. The hydrocarbon fuel can be a petroleum distillate to include a gasoline as defined by ASTM specification D4814 or a diesel fuel as defined by ASTM specification D975. In an embodiment of the invention the fuel is a gasoline, and in other embodiments the fuel is a leaded gasoline, or a nonleaded gasoline. In another embodiment of this invention the fuel is a diesel fuel. The hydrocarbon fuel can be a hydrocarbon prepared by a gas to liquid process to include for example hydrocarbons prepared by a process such as the Fischer-Tropsch process. The nonhydrocarbon fuel can be an oxygen containing composition, often referred to as an oxygenate, to include an alcohol, an ether, a ketone, an ester of a carboxylic acid, a nitroalkane, or a mixture thereof. The nonhydrocarbon fuel can include for example methanol, ethanol, methyl t-butyl ether, methyl ethyl ketone, transesterified oils and/or fats from plants and animals such as rapeseed methyl ester and soybean methyl ester, and nitromethane. Mixtures of hydrocarbon and nonhydrocarbon fuels can include for example gasoline and methanol and/or ethanol, diesel fuel and ethanol, and diesel fuel and a transesterified plant oil such as rapeseed methyl ester. In an embodiment of the invention the liquid fuel is an emulsion of water in a hydrocarbon fuel, a nonhydrocarbon fuel, or a mixture thereof. In several embodiments of this invention the fuel can have a sulphur content on a weight basis that is 5000 ppm or less, 1000 ppm or less, 300 ppm or less, 200 ppm or less, 30 ppm or less, or 10 ppm or less. In another embodiment the fuel can have a sulphur content on a weight basis of 1 to 100 ppm. In one embodiment the fuel contains about 0 ppm to about 1000 ppm, about 0 to about 500 ppm, about 0 to about 100 ppm, about 0 to about 50 ppm, about 0 to about 25 ppm, about 0 to about 10 ppm, or about 0 to 5 ppm of alkali metals, alkaline earth metals, transition metals or mixtures thereof. In another embodiment the fuel contains 1 to 10 ppm by weight of alkali metals, alkaline earth metals, transition metals or mixtures thereof. It is well known in the art that a fuel containing alkali metals, alkaline earth metals, transition metals or mixtures thereof have a greater tendency to form deposits and therefore foul or plug common rail injectors. The fuel of the invention is present in a fuel composition in a major amount that is generally greater than 50 percent by weight, and in other embodiments is present at greater than 90 percent by weight, greater than 95 percent by weight, greater than 99.5 percent by weight, or greater than 99.8 percent by weight.

The Quaternary Ammonium Salt

The quaternary ammonium salts of the present invention include the reaction product of: (i) a compound comprising at least one tertiary amino group and a hydrocarbyl-substituent derived from a hydrocarbon having a number average molecular weight of from about 100 to about 500, or from 100 to about 450, 150 to about 400, or 200 to about 350; and (ii) a quaternizing agent suitable for converting the tertiary amino group of compound (i) to a quaternary nitrogen.

The hydrocarbyl-substituent having a number average molecular weight of from about 100 to about 500, or from 100 to about 450, 150 to about 400, or 200 to about 350 can be, for example, a polyolefin, a polyalkene, or an ester or polyester. Example quaternary ammonium salts comprising a hydrocarbyl-substituent can therefore include, for example, the reaction product of: (i) at least one compound which may include: (a) the condensation product of a hydrocarbyl-substituted acylating agent and a compound having an oxygen or nitrogen atom capable of condensing the acylating agent where the condensation product has at least one tertiary amino group; (b) a polyalkene-substituted amine having at least one tertiary amino group; and (c) a polyester that is the reaction product of a fatty carboxylic acid containing at least one hydroxyl group and a compound having an oxygen or nitrogen atom capable of condensing with said acid where said compound contains a tertiary amino group; and (ii) a quaternizing agent suitable for converting the tertiary amino group compound of (i) to a quaternary nitrogen.

The quaternary ammonium salts of the present invention also include the reaction product of: (i) a compound comprising at least one tertiary amino group; and (ii) a quaternizing agent suitable for converting the tertiary amino group of compound (i) to a quaternary nitrogen.

Example quaternary ammonium salts can include, for example, the reaction product of: (i) at least one compound which may include: (d) a Mannich reaction product having at least one tertiary amino group, where the Mannich reaction product is derived from a hydrocarbyl-substituted phenol, an aldehyde, and an amine, (e) a non-quaternized amide and/or ester detergent having a tertiary amine functionality; and (ii) a quaternizing agent suitable for converting the tertiary amino group of compound (i) to a quaternary nitrogen.

The quaternizing agent may include dialkyl sulfates, benzyl halides, hydrocarbyl substituted carbonates, and hydrocarbyl epoxides, any of which may be used in combination with an acid.

The compounds of component (i)(a)-(i)(e), described in greater detail below, contain at least one tertiary amino group and include compounds that may be alkylated to contain at least one tertiary amino group after an alkylation step.

Examples of quaternary ammonium salts and methods for preparing the same are described in U.S. Pat. Nos. 4,253,980; 3,778,371; 4,171,959; 4,326,973; 4,338,206; and 5,254,138.

The quaternary ammonium salts may be prepared in the presence of a solvent, which may or may not be removed once the reaction is complete. Suitable solvents include, but are not limited to, diluent oil, petroleum naphtha, and certain alcohols. In one embodiment, these alcohols contain at least 2 carbon atoms, and in other embodiments at least 4, at least 6 or at least 8 carbon atoms. In another embodiment, the solvent of the present invention contains 2 to 20 carbon atoms, 4 to 16 carbon atoms, 6 to 12 carbon atoms, 8 to 10 carbon atoms, or just 8 carbon atoms. These alcohols often have a 2-($C_{1-4}$ alkyl) substituent, namely, methyl, ethyl, or any isomer of propyl or butyl. Examples of suitable alcohols include 2-propylheptanol, 2-methyldecanol, 2-ethylpentanol, 2-ethylhexanol, 2-ethylnonanol, 2-propylheptanol, 2-butylheptanol, 2-butyloctanol, isooctanol, dodecanol, cyclohexanol, methanol, ethanol, propan-1-ol, 2-methylpropan-2-ol, 2-methylpropan-1-ol, butan-1-ol, butan-2-ol, pentanol and its isomers, and mixtures thereof. In one embodiment the solvent of the present invention is 2-ethylhexanol, 2-ethyl nonanol, 2-methylheptanol, or combinations thereof. In one embodiment the solvent of the present invention includes 2-ethylhexanol.

Various embodiments of suitable quaternary ammonium salts are described herein and the invention contemplates the use of any one of them or combination thereof.

Succinimide Quaternary Ammonium Salts

In one embodiment the quaternary salt detergent comprises the reaction product of (i)(a) the condensation product of a hydrocarbyl-substituted acylating agent and a compound having an oxygen or nitrogen atom capable of condensing with said acylating agent where the condensation product has at least one tertiary amino group; and (ii) a quaternizing agent suitable for converting the tertiary amino group of compound (i) to a quaternary nitrogen.

Hydrocarbyl substituted acylating agents useful in the present invention include the reaction product of a short chain hydrocarbon, generally a polyolefin, with a monounsaturated carboxylic acid or derivative thereof.

Suitable monounsaturated carboxylic acids or derivatives thereof include: (i) α,β-monounsaturated $C_4$ to $C_{10}$ dicarboxylic acids, such as fumaric acid, itaconic acid, maleic acid; (ii) derivatives of (i), such as anhydrides or $C_1$ to $C_5$ alcohol derived mono- or di-esters of (i); (iii) α,β-monounsaturated $C_3$ to $C_{10}$ monocarboxylic acids, such as acrylic acid and methacrylic acid; or (iv) derivatives of (iii), such as $C_1$ to $C_5$ alcohol derived esters of (iii).

The short chain hydrocarbon for use in preparing the hydrocarbyl-substituted acylating agents can have a number average molecular weight of from about 100 to about 500, or from 100 to about 450, 150 to about 400, or 200 to about 350. Suitable hydrocarbons include any compound containing an olefinic bond represented by the general Formula I, shown here:

$$(R^1)(R^2)C=C(R^3)(CH(R^4)(R^5)) \qquad (I)$$

wherein each of $R^1$, $R^2$, $R^3$, $R^4$ and $R^5$ is, independently, hydrogen or a hydrocarbon based group. In some embodiments at least one of $R^3$, $R^4$ or $R^5$ is a hydrocarbon based group containing up to about 36 carbon atoms.

These short chain hydrocarbons, which may also be described as polyolefins or olefin polymers, are reacted with the monounsaturated carboxylic acids and derivatives described above to form the hydrocarbyl substituted acylating agents used to prepare the nitrogen-containing detergent of the present invention. Suitable olefin polymers include polymers comprising a major molar amount of $C_2$ to $C_{20}$, or $C_2$ to $C_5$ mono-olefins. Such olefins include ethylene, propylene, butylene, isobutylene, pentene, octene-1, or styrene. The polymers may be homo-polymers, such as polyisobutylene, as well as copolymers of two or more of such olefins. Suitable copolymers include copolymers of ethylene and propylene, butylene and isobutylene, and propylene and isobutylene. Other suitable copolymers include those in which a minor molar amount of the copolymer monomers, e.g. 1 to 10 mole %, is a $C_4$ to $C_{18}$ di-olefin. Such copolymers include: a copolymer of isobutylene and butadiene; and a copolymer of ethylene, propylene and 1,4-hexadiene.

In one embodiment, at least one of the —R groups of Formula (I) shown above is derived from polybutene, that is, polymers of $C_4$ olefins, including 1-butene, 2-butene and isobutylene. $C_4$ polymers include polyisobutylene. In another embodiment, at least one of the —R groups of Formula I is derived from ethylene-alpha olefin polymers, including ethylene-propylene-diene polymers. Examples of documents that described ethylene-alpha olefin copolymers and ethylene-lower olefin-diene ter-polymers include U.S. Pat. Nos. 3,598,738; 4,026,809; 4,032,700; 4,137,185; 4,156,061; 4,320,019; 4,357,250; 4,658,078; 4,668,834; 4,937,299; and 5,324,800.

In another embodiment, the olefinic bonds of Formula (I) are predominantly vinylidene groups, represented by the following formula:

wherein each R is a hydrocarbyl group; which in some embodiments may be:

wherein R is a hydrocarbyl group.

In one embodiment, the vinylidene content of Formula (I) may comprise at least 30 mole % vinylidene groups, at least 50 mole % vinylidene groups, or at least 70 mole % vinylidene groups. Such materials and methods of preparation are described in U.S. Pat. Nos. 5,071,919; 5,137,978; 5,137,980; 5,286,823, 5,408,018, 6,562,913, 6,683,138, 7,037,999; and United States publications: 2004/0176552A1; 2005/0137363; and 2006/0079652A1. Such products are commercially available from BASF, under the tradename GLISSOPAL™ and from Texas PetroChemical LP, under the tradename TPC 1105™ and TPC 595™.

Methods of making hydrocarbyl substituted acylating agents from the reaction of monounsaturated carboxylic acid reactants and compounds of Formula (I) are well known in the art and disclosed in: U.S. Pat. Nos. 3,361,673; 3,401,118; 3,087,436; 3,172,892; 3,272,746, 3,215,707; 3,231,587; 3,912,764; 4,110,349; 4,234,435; 6,077,909; and 6,165,235.

In another embodiment, the hydrocarbyl substituted acylating agent can be made from the reaction of a compound represented by Formula (I) with at least one carboxylic reactant represented by the following formulas:

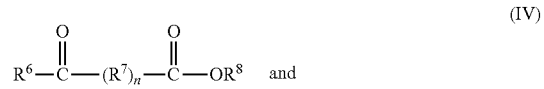

wherein each of $R^6$, $R^8$ and $R^9$ is independently H or a hydrocarbyl group, $R^7$ is a divalent hydrocarbylene group, and n is 0 or 1. Such compounds and the processes for making them are disclosed in U.S. Pat. Nos. 5,739,356; 5,777,142; 5,786,490; 5,856,524; 6,020,500; and 6,114,547.

In yet another embodiment, the hydrocarbyl substituted acylating agent may be made from the reaction of any compound represented by Formula (I) with any compound represented by Formula (IV) or Formula (V), where the reaction is carried out in the presence of at least one aldehyde or ketone. Suitable aldehydes include formaldehyde, acetaldehyde, propionaldehyde, butyraldehyde, isobutyraldehyde, pentanal, hexanal, heptaldehyde, octanal, benzaldehyde, as well as higher aldehydes. Other aldehydes, such as dialdehydes, especially glyoxal, are useful, although monoaldehydes are generally preferred. In one embodiment, the aldehyde is formaldehyde, which may be supplied in the aqueous solution often referred to as formalin, but which is more often used in the polymeric form referred to as paraformaldehyde. Paraformaldehyde is considered a reactive equivalent of and/or source of formaldehyde. Other reactive equivalents include hydrates or cyclic trimers. Suitable ketones include acetone, butanone, methyl ethyl ketone, as well as other ketones. In some embodiments, one of the two hydrocarbyl groups of the ketone is a methyl group. Mixtures of two or more aldehydes and/or ketones are also useful. Such hydrocarbyl substituted acylating agents and the processes for making them are disclosed in U.S. Pat. Nos. 5,840,920; 6,147,036; and 6,207,839.

In another embodiment, the hydrocarbyl substituted acylating agent may include methylene bis-phenol alkanoic acid compounds. Such compounds may be the condensation product of (i) an aromatic compound of the formula:

$$R_m\text{—Ar—}Z_c \qquad \text{(VI)}$$

and (ii) at least on carboxylic reactant such as the compounds of formula (IV) and (V) described above, wherein, in Formula (VI): each R is independently a hydrocarbyl group; m is 0 or an integer from 1 up to 6 with the proviso that m does not exceed the number of valences of the corresponding Ar group available for substitution; Ar is an aromatic group or moiety containing from 5 to 30 carbon atoms and from 0 to 3 optional substituents such as amino, hydroxy- or alkyl-polyoxyalkyl, nitro, aminoalkyl, and carboxy groups, or combinations of two or more of said optional substituents; Z is independently —OH, —O, a lower alkoxy group, or —$(OR^{10})_b OR_{11}$ wherein each $R^{10}$ is independently a divalent hydrocarbyl group, b is a number from 1 to 30, and $R^{11}$ is —H or a hydrocarbyl group; and c is a number ranging from 1 to 3.

In one embodiment, at least one hydrocarbyl group on the aromatic moiety is derived from polybutene. In one embodiment, the source of the hydrocarbyl groups described above are polybutenes obtained by polymerization of isobutylene in the presence of a Lewis acid catalyst such as aluminum trichloride or boron trifluoride. Such compounds and the processes for making them are disclosed in U.S. Pat. Nos. 3,954,808; 5,336,278; 5,458,793; 5,620,949; 5,827,805; and 6,001,781.

In another embodiment, the reaction of (i) with (ii), optionally in the presence of an acidic catalyst such as organic sulfonic acids, heteropolyacids, and mineral acids, can be carried out in the presence of at least one aldehyde or ketone. The aldehyde or ketone reactant employed in this embodiment is the same as those described above. Such compounds and the processes for making them are disclosed in U.S. Pat. No. 5,620,949. Still other methods of making suitable hydrocarbyl substituted acylating agents can be found in U.S. Pat. Nos. 5,912,213; 5,851,966; and 5,885,944.

The succinimide quaternary ammonium salt detergents are derived by reacting the hydrocarbyl substituted acylating agent described above with a compound having an oxygen or nitrogen atom capable of condensing with the acylating agent. In one embodiment, suitable compounds contain at least one tertiary amino group or may be alkylated until they contain a tertiary amino group, so long as the hydrocarbyl substituted acylating agent has at least one tertiary amino group when quaternized.

In one embodiment, this compound may be represented by one of the following formulas:

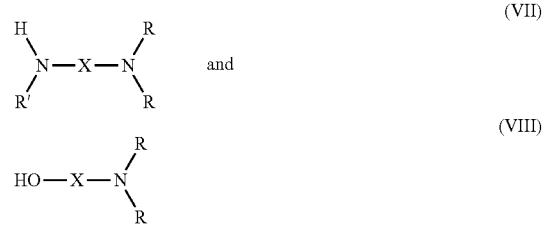

Wherein, for both Formulas (VII) and (VIII), each X is independently a alkylene group containing 1 to 4 carbon atoms; and each R is independently a hydrocarbyl group and R' is a hydrogen or a hydrocarbyl group.

Suitable compounds include but are not limited to: 1-aminopiperidine, 1-(2-aminoethyl)piperidine, 1-(3-aminopropyl)-2-pipecoline, 1-methyl-(4-methylamino)piperidine, 1-amino-2,6-dimethylpiperidine, 4-(1-pyrrolidinyl)piperidine, 1-(2-aminoethyl)pyrrolidine, 2-(2-aminoethyl)-1-methylpyrrolidine, N,N-diethylethylenediamine, N,N-dimethylethylenediamine, N,N-dibutylethylenediamine, N,N,N'-trimethylethylenediamine, N,N-dimethyl-N'-ethylethylenediamine, N,N-diethyl-N'-methylethylenediamine, N,N,N'-triethylethylenediamine, 3-dimethylaminopropylamine, 3-diethylaminopropylamine, 3-dibutylaminopropylamine, N,N,N'-trimethyl-1,3-propanediamine, N,N,2,2-tetramethyl-1,3-propanediamine, 2-amino-5-diethylaminopentane, N,N,N',N'-tetraethyldiethylenetriamine, 3,3'-diamino-N-methyldipropylamine, 3,3'-iminobis(N,N-dimethylpropylamine), or combinations thereof. In some embodiments the amine used is 3-dimethylaminopropylamine, 3-diethylamino-propylamine, 1-(2-aminoethyl)pyrrolidine, N,N-dimethylethylenediamine, N,N-diethylpropylenediamine or combinations thereof.

Suitable compounds further include aminoalkyl substituted heterocyclic compounds such as 1-(3-aminopropyl) imidazole and 4-(3-aminopropyl)morpholine, 1-(2-aminoethyl)piperidine, 3,3-diamino-N-methyldipropylamine, 3,3'-aminobis(N,N-dimethylpropylamine) These have been mentioned in previous list.

Still further nitrogen or oxygen containing compounds capable of condensing with the acylating agent which also have a tertiary amino group include: alkanolamines, including but not limited to triethanolamine, trimethanolamine, N,N-dimethylaminopropanol, N,N-diethylaminopropanol, N,N-diethylaminobutanol, N,N,N-tris(hydroxyethyl)amine, and N,N,N-tris(hydroxymethyl)amine.

The succinimide quaternary ammonium salt detergents of the present invention are formed by combining the reaction product described above (the reaction product of a hydrocarbyl-substituted acylating agent and a compound having an oxygen or nitrogen atom capable of condensing with said acylating agent and further having at least one tertiary amino group) with a quaternizing agent suitable for converting the tertiary amino group to a quaternary nitrogen. Suitable quaternizing agents are discussed in greater detail below. In some embodiments these preparations may be carried out neat or in the presence of a solvent, as described above. By way of non-limiting example, preparations of succinimide quaternary ammonium salts are provided below.

In some embodiments the compositions of the invention are substantially free of, or even completely free of, the succinimide quaternary ammonium salts described above.

Polyalkene-Substituted Amine Quaternary Ammonium Salts

In one embodiment the quaternary ammonium salt is the reaction product of: (i)(b) a hydrocarbyl-substituted amine having at least one tertiary amino group; and (ii) a quaternizing agent suitable for converting the tertiary amino group of compound (i) to a quaternary nitrogen, wherein the hydrocarbyl-substituent is a polyalkene-substituent having a number average molecular weight of from about 100 to about 500, or 100 to 450, or 150 to 400 or 200 to 350.

Suitable polyalkene-substituted amines may be derived from an olefin polymer and an amine, such as ammonia, monoamines, polyamines or mixtures thereof. They may be prepared by a variety of methods. Suitable polyalkene-substituted amines or the amines from which they are derived either contain a tertiary amino group or may be alkylated until they contain a tertiary amino group, so long as the polyalkene-substituted amine has at least one tertiary amino group when it is quaternized.

One method of preparation of a polyalkene-substituted amine involves reacting a halogenated olefin polymer with an amine, as disclosed in U.S. Pat. Nos. 3,275,554; 3,438,757; 3,454,555; 3,565,804; 3,755,433; and 3,822,289. Another method of preparation of a polyalkene-substituted amine involves reaction of a hydro-formylated olefin with a polyamine and hydrogenating the reaction product, as disclosed in U.S. Pat. Nos. 5,567,845 and 5,496,383. Another method for preparing a polyalkene-substituted amine involves converting a polyalkene, by means of a conventional epoxidation reagent, with or without a catalyst, into the corresponding epoxide and converting the epoxide into the polyalkene substituted amine by reaction with ammonia or an amine under the conditions of reductive amination, as disclosed in U.S. Pat. No. 5,350,429. Another method for preparing a polyalkene-substituted amine involves hydrogenation of a β-aminonitrile, made by reacting an amine with a nitrile, as disclosed in U.S. Pat. No. 5,492,641. Yet another method for preparing a polyalkene-substituted amine involves hydroformylating polybutene or polyisobutylene, with a catalyst, such as rhodium or cobalt, in the presence of CO, $H_2$ and $NH_3$ at elevated pressures and temperatures, as disclosed in U.S. Pat. Nos.: 4,832,702; 5,496,383 and 5,567,845. The above methods for the preparation of polyalkene substituted amine are for illustrative purposes only and are not meant to be an exhaustive list. The polyalkene-substituted amines of the present invention are not limited in scope to the methods of their preparation disclosed hereinabove.

The polyalkene-substituted amine may be derived from olefin polymers. Suitable olefin polymers for preparing the polyalkene-substituted amines of the invention are the same as those described above.

The polyalkene-substituted amine may be derived from ammonia, monoamines, polyamines, or mixtures thereof, including mixtures of different monoamines, mixtures of different polyamines, and mixtures of monoamines and polyamines (which include diamines). Suitable amines include aliphatic, aromatic, heterocyclic and carbocyclic amines.

In one embodiment, the amines may be characterized by the formula:

$$R^{12}R^{13}NH \qquad (IX)$$

wherein $R^{12}$ and $R^{13}$ are each independently hydrogen, hydrocarbon, amino-substituted hydrocarbon, hydroxy-substituted hydrocarbon, alkoxy-substituted hydrocarbon, or acylimidoyl groups provided that no more than one of $R^{12}$ and $R^{13}$ is hydrogen. The amine may be characterized by the presence of at least of at least one primary ($H_2N$—) or secondary amino (H—N<) group. These amines, or the polyalkene-substituted amines they are used to prepare may be alkylated as needed to ensure they contain at least one tertiary amino group. Examples of suitable monoamines include ethylamine, dimethylamine, diethylamine, n-butylamine, dibutylamine, allylamine, isobutylamine, cocoamine, stearylamine, laurylamine, methyllaurylamine, oleylamine, N-methyl-octylamine, dodecyl-amine, diethanolamine, morpholine, and octadecylamine.

The polyamines from which the detergent is derived include principally alkylene amines conforming, for the most part, to the formula:

$$(X)$$

wherein n is an integer typically less than 10, each $R^{14}$ is independently hydrogen or a hydrocarbyl group typically having up to 30 carbon atoms, and the alkylene group is typically an alkylene group having less than 8 carbon atoms. The alkylene amines include principally, ethylene amines, hexylene amines, heptylene amines, octylene amines, other polymethylene amines. They are exemplified specifically by: ethylenediamine, diethylenetriamine, triethylene tetramine, propylene diamine, decamethylene diamine, octamethylene diamine, di(heptamethylene) triamine, tripropylene tetramine, tetraethylene pentamine, trimethylene diamine, pentaethylene hexamine, di(-trimethylene)triamine, aminopropylmorpholine and dimethylaminopropylamine. Higher homologues such as are obtained by condensing two or more of the above-illustrated alkylene amines likewise are useful. Tetraethylene pentamine is particularly useful.

The ethylene amines, also referred to as polyethylene polyamines, are especially useful. They are described in some detail under the heading "Ethylene Amines" in Encyclopedia of Chemical Technology, Kirk and Othmer, Vol. 5, pp. 898-905, Interscience Publishers, New York (1950).

Any of the above polyalkene-substituted amines, or the amines from which they are derived, which are secondary or primary amines, may be alkylated to tertiary amines using alkylating agents before or while they are reacted with the quaternizing agents to form the quaternary ammonium salt additives of the present invention. Suitable alkylating agents include the quaternizing agents discussed below.

The polyalkene-substituted amine quaternary ammonium salts of the present invention are formed by combining the reaction product described above (the polyalkene-substituted amine, having at least one tertiary amino group) with a quaternizing agent suitable for converting the tertiary amino group to a quaternary nitrogen. Suitable quaternizing agents are discussed in greater detail below. By way of non-limiting example, a preparation of a polyalkene-substituted amine quaternary ammonium salt is provided below.

In some embodiments the compositions of the invention are substantially free of, or even completely free of, the polyalkene-substituted amine quaternary ammonium salts described above.

Polyester Quaternary Ammonium Salts

In some embodiments the hydrocarbyl-substituent of the quaternary ammonium salt is a polyester having a number average molecular weight of from about 100 to about 500, or 100 to 450, or 150 to 400 or 200 to 350. The polyester quaternary salt may include quaternized polyester amine, amide, and ester salts. Such additives may also be described as quaternary polyester salts. The additives of the invention may be described as the reaction product of: a polyester containing a tertiary amino group; and a quaternizing agent suitable for converting the tertiary amino group to a quaternary nitrogen. The quaternary agents may be any of the agents described hereinabove.

The polyester containing a tertiary amino group used in the preparation of the additives of the invention may also be described as a non-quaternized polyester containing a tertiary amino group.

In some embodiments the polyester is the reaction product of a fatty carboxylic acid containing at least one hydroxyl group and a compound having an oxygen or nitrogen atom capable of condensing with said acid further having a tertiary amino group. Suitable fatty carboxylic acids to use in the preparation of the polyesters described above may be represented by the formula:

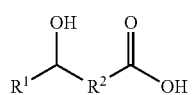
(XI)

where $R^1$ is a hydrogen or a hydrocarbyl group containing from 1 to 20 carbon atoms and $R^2$ is a hydrocarbylene group containing from 1 to 20 carbon atoms. In some embodiments $R^1$ contains from 1 to 12, 2 to 10, 4 to 8 or even 6 carbon atoms, and $R^2$ contains from 2 to 16, 6 to 14, 8 to 12, or even 10 carbon atoms.

In some embodiments the fatty carboxylic acid used in the preparation of the polyester is 12-hydroxystearic acid, ricinoleic acid, 12-hydroxy dodecanoic acid, 5-hydroxy dodecanoic acid, 5-hydroxy decanoic acid, 4-hydroxy decanoic acid, 10-hydroxy undecanoic acid, or combinations thereof.

In some embodiments the compound having an oxygen or nitrogen atom capable of condensing with said acid and further having a tertiary amino group is represented by the formula:

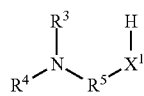
(XII)

where $R^3$ is a hydrocarbyl group containing from 1 to 10 carbon atoms; $R^4$ is a hydrocarbyl group containing from 1 to 10 carbon atoms; $R^5$ is a hydrocarbylene group containing from 1 to 20 carbon atoms; and $X^1$ is O or $NR^6$ where $R^6$ is a hydrogen or a hydrocarbyl group containing from 1 to 10 carbon atoms. In some embodiments $R^3$ contains from 1 to 6, 1 to 2, or even 1 carbon atom, $R^4$ contains from 1 to 6, 1 to 2, or even 1 carbon atom, $R^5$ contains from 2 to 12, 2 to 8 or even 3 carbon atoms, and $R^6$ contains from 1 to 8, or 1 to 4 carbon atoms. In some of these embodiments, formula (XII) becomes:

(XII-a)

or

(XII-b)

where the various definitions provided above still apply.

Examples of nitrogen or oxygen containing compounds capable of condensing with the acylating agents, which also have a tertiary amino group, or compounds that can be alkylated into such compounds, include any of the materials described in the sections above.

The nitrogen or oxygen containing compounds may further include aminoalkyl substituted heterocyclic compounds such as 1-(3-aminopropyl)imidazole and 4-(3-aminopropyl) morpholine.

In one embodiment the nitrogen or oxygen containing compound is triisopropanolamine, 1-[2-hydroxyethyl]piperidine, 2-[2-(dimethylamino)ethoxy]-ethanol, N-ethyldiethanolamine, N-methyldiethanolamine, N-butyldiethanolamine, N,N-diethylamino ethanol, N,N-dimethylaminoethanol, 2-dimethylamino-2-methyl-1-propanol, or combinations thereof.

In some embodiments the compound having an oxygen or nitrogen atom capable of condensing with said acid and further having a tertiary amino group comprises N,N-diethylethylenediamine, N,N-dimethylethylenediamine, N,N-dibutylethylenediamine, N,N-dimethyl-1,3-diaminopropane, N,N-diethyl-1,3-diaminopropane, N,N-dimethylaminoethanol, N,N-diethylaminoethanol, N,N-diethylpropylenediamine or combinations thereof.

The quaternized polyester salt can be a quaternized polyester amide salt. In such embodiments the polyester containing a tertiary amino group used to prepare the quaternized polyester salt is a polyester amide containing a tertiary amino group. In some of these embodiments the amine or amino alcohol is reacted with a monomer and then the resulting material is polymerized with additional monomer, giving the polyester amide which may then be quaternized.

In some embodiments the quaternized polyester salt includes a cation represented by the following formula:

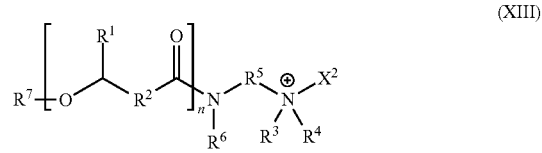
(XIII)

where $R^1$ is a hydrogen or a hydrocarbyl group containing from 1 to 3 carbon atoms and $R^2$ is a hydrocarbylene group containing from 1 to 4 carbon atoms; $R^3$ is a hydrocarbyl group containing from 1 to 3 carbon atoms; $R^4$ is a hydrocarbyl group containing from 1 to 3 carbon atoms; $R^5$ is a hydrocarbylene group containing from 1 or 2 to 6 carbon atoms; $R^6$ is a hydrogen or a hydrocarbyl group containing from 1 to 3 carbon atoms; n is a number from 1 to about 7 or from 1 to about 5; $R^7$ is hydrogen, a hydrocarbonyl group containing from 1 to 3 carbon atoms, or a hydrocarbyl group containing from 1 to 3 carbon atoms; and $X^2$ is a group derived from the quaternizing agent. In some embodiments $R^6$ is hydrogen.

As above, in some embodiments $R^1$ contains from 1 to 2, 2 to 3, or 1 carbon atoms, and $R^2$ contains from 1 to 2, or 2 to 3, or 1 carbon atoms, $R^3$ contains from 1 to 2, 2 to 3, or even 1 carbon atom, $R^4$ contains from 1 to 2, 2 to 3, or even 1 carbon atom, $R^5$ contains from 1 to 2, 2 to 3 or even 1 carbon atoms, and $R^6$ contains from 1 to 2, or 2 to 3, or even 1 carbon atoms. In any of these embodiments n may be from 2 to 7, or 3 to 6, and $R^7$ may contain from 1 to 2, or 2 to 3, or 1 carbon atoms. $R^7$ may be an acyl group.

In these embodiments the quaternized polyester salt is essentially capped with a C1-22, or a C8-20, fatty acid. Examples of suitable acids include oleic acid, palmitic acid, stearic acid, erucic acid, lauric acid, 2-ethylhexanoic acid, 9,11-linoleic acid, 9,12-linoleic acid, 9,12,15-linolenic acid, abietic acid, or combinations thereof.

The number average molecular weight (Mn) of the fully quaternized polyester salts of the invention may be from about 100 to about 750, or from about 200 to about 700, or from about 100 to about 500.

The polyester useful in the present invention can be obtained by heating one or more hydroxycarboxylic acids or a mixture of the hydroxycarboxylic acid and a carboxylic acid, optionally in the presence of an esterification catalyst. The hydroxycarboxylic acids can have the formula HO—X—COOH wherein X is a divalent saturated or unsaturated aliphatic radical containing at least 8 carbon atoms and in which there are at least 4 carbon atoms between the hydroxy and carboxylic acid groups, or from a mixture of such a hydroxycarboxylic acid and a carboxylic acid which is free from hydroxy groups. This reaction can be carried out at a temperature in the region of 160 C to 200 C, until the desired molecular weight has been obtained. The course of the esterification can be followed by measuring the acid value of the product, with the desired polyester, in some embodiments, having an acid value in the range of 1 to 200 mg KOH/g or in the range of 10 to 150 mg KOH/g. The indicated acid value range of 1 to 200 mg KOH/g is equivalent to a number average molecular weight range of 56100 to 280. The water formed in the esterification reaction can be removed from the reaction medium, and this can be conveniently done by passing a stream of nitrogen over the reaction mixture or, by carrying out the reaction in the presence of a solvent, such as toluene or xylene, and distilling off the water as it is formed.

The resulting polyester can then be isolated in conventional manner; however, when the reaction is carried out in the presence of an organic solvent whose presence would not be harmful in the subsequent application, the resulting solution of the polyester can be used.

In the said hydroxycarboxylic acids the radical represented by X may contain from 12 to 20 carbon atoms, optionally where there are between 8 and 14 carbon atoms between the carboxylic acid and hydroxy groups. In some embodiments the hydroxy group is a secondary hydroxy group.

Specific examples of such hydroxycarboxylic acids include ricinoleic acid, a mixture of 9- and 10-hydroxystearic acids (obtained by sulphation of oleic acid and then hydrolysis), and 12-hydroxystearic acid, and the commercially available hydrogenated castor oil fatty acid which contains in addition to 12-hydroxystearic acid minor amounts of stearic acid and palmitic acid.

The carboxylic acids which can be used in conjunction with the hydroxycarboxylic acids to obtain these polyesters are preferably carboxylic acids of saturated or unsaturated aliphatic compounds, particularly alkyl and alkenyl carboxylic acids containing a chain of from 8 to 20 carbon atoms. As examples of such acids there may be mentioned lauric acid, palmitic acid, stearic acid and oleic acid.

In one embodiment the polyester is derived from commercial 12-hydroxy-stearic acid having a number average molecular weight of about 1600. Polyesters such as this are described in greater detail in U.K. Patent Specification Nos. 1373660 and 1342746.

In some embodiments the components used to prepare the additives described above are substantially free of, essentially free of, or even completely free of, non-polyester-containing hydrocarbyl substituted acylating agents and/or non-polyester-containing hydrocarbyl substituted diacylating agents, such as for example polyisobutylene. In some embodiments these excluded agents are the reaction product of a long chain hydrocarbon, generally a polyolefin reacted with a monounsaturated carboxylic acid reactant, such as, (i) α,β-monounsaturated $C_4$ to $C_{10}$ dicarboxylic acid, such as, fumaric acid, itaconic acid, maleic acid.; (ii) derivatives of (i) such as anhydrides or $C_1$ to $C_5$ alcohol derived mono- or di-esters of (i); (iii) α,β-monounsaturated $C_3$ to $C_{10}$ monocarboxylic acid such as acrylic acid and methacrylic acid.; or (iv) derivatives of (iii), such as, $C_1$ to $C_5$ alcohol derived esters of (iii) with any compound containing an olefinic bond represented by the general formula $(R^9)(R^{10})C=C(R^{11})(CH(R^7)(R^8))$ wherein each of $R^9$ and $R^{10}$ is independently hydrogen or a hydrocarbon based group; each of $R^{11}$, $R^7$ and $R^8$ is independently hydrogen or a hydrocarbon based group and preferably at least one is a hydrocarbyl group containing at least 20 carbon atoms. In one embodiment, the excluded hydrocarbyl-substituted acylating agent is a dicarboxylic acylating agent. In some of these embodiments, the excluded hydrocarbyl-substituted acylating agent is polyisobutylene succinic anhydride.

By substantially free of, it is meant that the components of the present invention are primarily composed of materials other than hydrocarbyl substituted acylating agents described above such that these agents are not significantly involved in the reaction and the compositions of the invention do not contain significant amounts of additives derived from such agents. In some embodiments the components of the invention, or the compositions of the invention, may contain less than 10 percent by weight of these agents, or of the additives derived from these agents. In other embodiments the maximum allowable amount may be 5, 3, 2, 1 or even 0.5 or 0.1 percent by weight. One of the purposes of these embodiments is to allow the exclusion of agents such as polyisobutylene succinic anhydrides from the reactions of the invention and so, to also allow the exclusion of quaternized salt detergent additive derived from agents such as polyisobutylene succinic anhydrides. The focus of this embodiment is on polyester, or hyperdispersant, quaternary salt detergent additives.

In some embodiments the compositions of the invention are substantially free of, or even completely free of, the polyester quaternary salts described above.

Mannich Quaternary Ammonium Salts

In one embodiment the quaternary ammonium salt is the reaction product of: (i)(c) a Mannich reaction product; and (ii) a quaternizing agent suitable for converting the tertiary amino group of compound (i) to a quaternary nitrogen.

Suitable Mannich reaction products have at least one tertiary amino group and are prepared from the reaction of a hydrocarbyl-substituted phenol, an aldehyde, and an amine.

The hydrocarbyl substituent of the hydrocarbyl-substituted phenol can have 1 to 36 carbon atoms, in another instance 2 to 34 carbon atoms, and in a further instance 5 or 8 to 30 carbon atoms. This hydrocarbyl substituent can be derived from an olefin or a polyolefin. Useful olefins include alpha-olefins, such as 1-decene, which are commercially available. Suitable polyolefins include those described in the sections above. The hydrocarbyl-substituted phenol can be prepared by alkylating phenol with one of these suitable olefins or polyolefins, such as a polyisobutylene or polypropylene, using well-known alkylation methods.

The aldehyde used to form the Mannich detergent can have 1 to 10 carbon atoms, and is generally formaldehyde or a reactive equivalent thereof, such as formalin or paraformaldehyde.

The amine used to form the Mannich detergent can be a monoamine or a polyamine. Amines suitable for preparing the Mannich reaction product of the invention are the same as those are described in the sections above.

In one embodiment, the Mannich detergent is prepared by reacting a hydrocarbyl-substituted phenol, an aldehyde, and an amine, as described in U.S. Pat. No. 5,697,988. In one embodiment, the Mannich reaction product is prepared from: an alkylphenol derived from a polyisobutylene; formaldehyde; and a primary monoamine, secondary monoamine, or alkylenediamine. In some of such embodiments the amine is ethylenediamine or dimethylamine. Other methods of preparing suitable Mannich reaction products can be found in U.S. Pat. Nos. 5,876,468 and 5,876,468.

As discussed above, it may be necessary, with some of the amines, to further react the Mannich reaction product with an epoxide or carbonate, or other alkylating agent, in order to obtain the tertiary amino group.

The Mannich quaternary ammonium salts of the present invention are formed by combining the reaction product described above (the Mannich reaction product with at least one tertiary amino group) with a quaternizing agent suitable for converting the tertiary amino group to a quaternary nitrogen. Suitable quaternizing agents are discussed below.

In some embodiments the compositions of the invention are substantially free of, or even completely free of, the Mannich quaternary ammonium salts described above.

Amide and/or Ester Quaternary Ammonium Salts

In some embodiments the quaternary ammonium salts used in the invention are quaternary amide and/or ester detergents which may be described as the reaction product of: (i) a non-quaternized amide and/or ester detergent having a tertiary amine functionality; and (ii) a quaternizing agent. In some embodiments the non-quaternized detergent is the condensation product of (a) a hydrocarbyl-substituted acylating agent and (b) a compound having an oxygen or nitrogen atom capable of condensing with said acylating agent and further having at least one tertiary amino group.

The non-quaternized amide and/or ester detergents suitable for use in the present invention include the condensation product of (i) a hydrocarbyl-substituted acylating agent and (ii) a compound having an oxygen or nitrogen atom capable of condensing with said acylating agent and further having at least one tertiary amino group, where the resulting detergent has at least one tertiary amino group and also contains an amide group and/or an ester group. Typically, the compound having an oxygen or nitrogen atom capable of condensing with said acylating agent determines whether the resulting detergent contains an amide group or an ester group. In some embodiments, the non-quaternized detergent, and so the resulting quaternized detergent is free of any imide groups. In some embodiments, the non-quaternized detergent, and so the resulting quaternized detergent is free of any ester groups. In these embodiments the detergent contains at least one, or just one, amide group.

The hydrocarbyl substituted acylating agent can be any of the materials described in section above provided that the material contains an amide group and/or an ester group.

The non-quaternized amide and/or ester detergent used to prepare the additives of the present invention are themselves formed when the acylating agents described above are reacted with a compound having an oxygen or nitrogen atom capable of condensing with the acylating agent which further has at least one tertiary amino group. Any of these compounds described above may be used here as well.

In one embodiment, the non-quaternized amide and/or ester group can comprise a hydrocarbyl substituted dicarboxylic acid, for example, a succinic acid, free of any imide groups, wherein one of the carboxylic acid moieties reacts with the compound having an oxygen or nitrogen atom capable of condensing with the acylating agent to form an amide and the other carboxylic acid moiety remains an acid group. In another embodiment, the non-quaternized amide and/or ester group can comprise a hydrocarbyl substituted dicarboxylic acid, for example, a succinic acid, free of any anhydride groups, wherein one of the carboxylic acid moieties reacts with the compound having an oxygen or nitrogen atom capable of condensing with the acylating agent to form an ester and the other carboxylic acid moiety remains an acid group.

In further embodiments, the non-quaternized amide and/or ester group can be represented by the following formula:

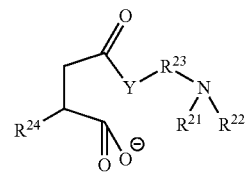

wherein: $R^{21}$ is a hydrocarbyl group containing from 1 to 3 carbon atoms; $R^{22}$ is a hydrocarbyl group containing from 1 to 3 carbon atoms; $R^{23}$ is a hydrocarbylene group containing from 1 to 3 carbon atoms; $R^{24}$ is a hydrocarbyl group containing from 7 to 36 carbon atoms; and Y is NH or O.

The quaternary amide and/or ester detergents are prepared by reacting (a) the non-quaternized amide and/or ester detergent having a tertiary amine functionality with (b) the quaternizing agent; thereby obtaining the quaternized detergent. The processes of the present invention may also be described as a process for preparing a quaternized amide and/or ester detergent comprising the steps of: (1) mixing (a) a non-quaternized amide and/or ester detergent having an amine functionality, (b) a quaternizing agent and optionally with (c) a protic solvent, which in some embodiments is free of methanol; (2) heating the mixture to a temperature between 50° C. to 130° C.; and (3) holding for the reaction to complete; thereby obtaining the quaternized amide and/or ester detergent. In one embodiment the reaction is carried out at a temperature of less than 80° C., or less than 70° C. In other embodiments the reaction mixture is heated to a temperature of about 50° C. to 120° C., 80° C., or 70° C. In still other embodiments where the hydrocarbyl acylating agent is derived from a monocarboxylic acid, the reaction temperature may be 70° C. to 130° C. In other embodiments where the hydrocarbyl acylating agent is derived from a dicarboxylic acid, the reaction temperature may be 50° C. to 80° C. or 50° C. to 70° C. In some embodiments the processes of the present invention are free of the addition of any acid reactant, such as acetic acid. The salt product is obtained in these embodiments despite the absence of the separate acid reactant.

As described above, in some embodiments the non-quaternized amide and/or ester detergent is the condensation product of hydrocarbyl-substituted acylating agent and a compound having an oxygen or nitrogen atom capable of condensing with said acylating agent and further having at least one tertiary amino group. Suitable quaternizing agents and compounds having an oxygen or nitrogen atom are also described above.

The additives of the present invention may be derived in the presence of a protic solvent. In some embodiments the process used to prepare these additives is substantially free of to free of methanol. Substantially free of methanol can mean less than 0.5, 0.1 or 0.05 percent by weight methanol in the reaction mixture, and may also mean completely free of methanol.

Suitable protic solvents include solvents that have dielectric constants of greater than 9. In one embodiment the protic solvent includes compounds that contain 1 or more hydroxyl functional groups, and may include water.

In one embodiment, the solvents are glycols and glycol ethers. Glycols containing from 2 to 12 carbon atoms, or from 4 to 10, or 6 to 8 carbon atoms, and oligomers thereof (e.g., dimers, trimers and tetramers) are generally suitable for use. Illustrative glycols include ethylene glycol, propylene glycol, diethylene glycol, dipropylene glycol, 1,4-butanediol, 2-methyl-1,3-propanediol, neopentyl glycol, triethylene glycol, polyethylene glycol and the like and oligomers and polymeric derivative and mixtures thereof. Illustrative glycol ethers include the $C_1$-$C_6$ alkyl ethers of propylene glycol, ethylene glycol and oligomers thereof such as di-, tri- and tetra glycol ethers of methyl, ethyl, propyl, butyl or hexyl. Suitable glycol ethers include ethers of dipropylene glycol, tripropylene glycol diethylene glycol, triethylene glycol; ethyl diglycol ether, butyl diglycol ether, methoxytriglycol, ethoxytriglycol, butoxytriglycol, methoxytetraglycol, butoxytetraglycol.

Suitable solvents for use in the invention also include certain alcohols. In one embodiment, these alcohols contain at least 2 carbon atoms, and in other embodiments at least 4, at least 6 or at least 8 carbon atoms. In another embodiment, the solvent of the present invention contains 2 to 20 carbon atoms, 4 to 16 carbon atoms, 6 to 12 carbon atoms, 8 to 10 carbon atoms, or just 8 carbon atoms. These alcohols normally have a 2-($C_{1-4}$ alkyl) substituent, namely, methyl, ethyl, or any isomer of propyl or butyl. Examples of suitable alcohols include 2-methylheptanol, 2-methyldecanol, 2-ethylpentanol, 2-ethylhexanol, 2-ethylnonanol, 2-propylheptanol, 2-butylheptanol, 2-butyloctanol, isooctanol, dodecanol, cyclohexanol, methanol, ethanol, propan-1-ol, 2-methylpropan-2-ol, 2-methylpropan-1-ol, butan-1-ol, butan-2-ol, pentanol and its isomers, and mixtures thereof. In one embodiment the solvent of the present invention is 2-ethylhexanol, 2-ethyl nonanol, 2-propylheptanol, or combinations thereof. In one embodiment the solvent of the present invention includes 2-ethylhexanol.

The solvent can be any of the commercially available alcohols or mixtures of such alcohols and also includes such alcohols and mixtures of alcohols mixed with water. In some embodiments the amount of water present may be above 1 percent by weight of the solvent mixture. In other embodiments the solvent mixture may contain traces of water, with the water content being less than 1 or 0.5 percent by weight.

The alcohols can be aliphatic, cycloaliphatic, aromatic, or heterocyclic, including aliphatic-substituted cycloaliphatic alcohols, aliphatic-substituted aromatic alcohols, aliphatic-substituted heterocyclic alcohols, cycloaliphatic-substituted aliphatic alcohols, cycloaliphatic-substituted aromatic alcohols, cycloaliphatic-substituted heterocyclic alcohols, heterocyclic-substituted aliphatic alcohols, heterocyclic-substituted cycloaliphatic alcohols, and heterocyclic-substituted aromatic alcohols.

While not wishing to be bound by theory, it is believed that a polar protic solvent is required in order to facilitate the dissociation of the acid into ions and protons. The dissociation is required to protonate the ion formed when the detergent having an amine functionality initially reacts with the quaternizing agent. In the case where the quaternizing agent is an alkyl epoxide the resulting ion would be an unstable alkoxide ion. The dissociation also provides a counter ion from the acid group of the additive that acts to stabilize the quaternary ammonium ion formed in the reaction, resulting in a more stable product.

The solvent may be present such that the weight ratio of the amount of detergent having an amine functionality to the amount of polar solvent is in one set of embodiments from 20:1 to 1:20; or from 10:1 to 1:10. In additional embodiments, the detergent to solvent weight ratio can be from 1:10 to 1:15; from 15:1 to 10:1; or from 5:1 to 1:1.

In some embodiments the compositions of the invention are substantially free of, or even completely free of, the quaternary amide and/or ester detergents described above.

The Quaternizing Agent

Suitable quaternizing agents for preparing any of the quaternary ammonium salt detergents described above include dialkyl sulfates, benzyl halides, hydrocarbyl substituted carbonates, hydrocarbyl epoxides used in combination with an acid, esters of polycarboxylic acids, or mixtures thereof.

In one embodiment the quaternizing agent includes: halides such as chloride, iodide or bromide; hydroxides; sulphonates; alkyl sulphates such as dimethyl sulphate; sultones; phosphates; $C_{1-12}$ alkylphosphates; di-$C_{1-12}$ alkylphosphates; borates; $C_{1-12}$ alkylborates; nitrites; nitrates; carbonates; bicarbonates; alkanoates; O,O-di-$C_{1-12}$ alkyldithiophosphates; or mixtures thereof.

In one embodiment the quaternizing agent may be: a dialkyl sulphate such as dimethyl sulphate; N-oxides; sultones such as propane or butane sultone; alkyl, acyl or aralkyl halides such as methyl and ethyl chloride, bromide or iodide or benzyl chloride; hydrocarbyl (or alkyl) substituted carbonates; or combinations thereof. If the aralkyl halide is benzyl chloride, the aromatic ring is optionally further substituted with alkyl or alkenyl groups.

The hydrocarbyl (or alkyl) groups of the hydrocarbyl substituted carbonates may contain 1 to 50, 1 to 20, 1 to 10 or 1 to 5, or 1 to 3 carbon atoms per group. In one embodiment the hydrocarbyl substituted carbonates contain two hydrocarbyl groups that may be the same or different. Examples of suitable hydrocarbyl substituted carbonates include dimethyl or diethyl carbonate.

In another embodiment the quaternizing agent can be a hydrocarbyl epoxides, as represented by the following formula:

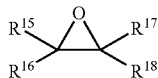 (XIV)

wherein $R^{15}$, $R^{16}$, $R^{17}$ and $R^{18}$ can be independently H or a $C_{1-50}$ hydrocarbyl group. Examples of suitable hydrocarbyl epoxides include: styrene oxide, ethylene oxide, propylene oxide, butylene oxide, stilbene oxide, $C_{2-50}$ epoxides, or combinations thereof.

In another embodiment the quaternizing agent can be an ester of a carboxylic acid capable of reacting with a tertiary amine to form a quaternary ammonium salt, or an ester of a polycarboxylic acid. In a general sense such materials may be described as compounds having the structure:

$$R^{19}-C(=O)-O-R^{20} \qquad (XV)$$

where $R^{19}$ is an optionally substituted alkyl, alkenyl, aryl or alkylaryl group and $R^{20}$ is a hydrocarbyl group containing from 1 to 22 carbon atoms.

Suitable compounds include esters of carboxylic acids having a pKa of 3.5 or less. In some embodiments the compound is an ester of a carboxylic acid selected from a substituted aromatic carboxylic acid, an a-hydroxycarboxylic acid and a polycarboxylic acid. In some embodiments the compound is an ester of a substituted aromatic carboxylic acid and thus $R^{19}$ is a substituted aryl group. R may be a substituted aryl group having 6 to 10 carbon atoms, a phenyl group, or a naphthyl group. R may be suitably substituted with one or more groups selected from carboalkoxy, nitro, cyano, hydroxy, SR' or NR'R" where each of R' and R" may independently be hydrogen, or an optionally substituted alkyl, alkenyl, aryl or carboalkoxy groups. In some embodiments R' and R" are each independently hydrogen or an optionally substituted alkyl group containing from 1 to 22, 1 to 16, 1 to 10, or even 1 to 4 carbon atoms.

In some embodiments $R^{19}$ in the formula above is an aryl group substituted with one or more groups selected from hydroxyl, carboalkoxy, nitro, cyano and $NH^2$. $R^{19}$ may be a poly-substituted aryl group, for example trihydroxyphenyl, but may also be a mono-substituted aryl group, for example an ortho substituted aryl group. $R^{19}$ may be substituted with a group selected from OH, $NH_2$, $NO_2$, or COOMe. Suitably $R^{19}$ is a hydroxy substituted aryl group. In some embodiments $R^{19}$ is a 2-hydroxyphenyl group. $R^{20}$ may be an alkyl or alkylaryl group, for example an alkyl or alkylaryl group containing from 1 to 16 carbon atoms, or from 1 to 10, or 1 to 8 carbon atoms. $R^{20}$ may be methyl, ethyl, propyl, butyl, pentyl, benzyl or an isomer thereof. In some embodiments $R^{20}$ is benzyl or methyl. In some embodiments the quaternizing agent is methyl salicylate.

In some embodiments the quaternizing agent is an ester of an alpha-hydroxycarboxylic acid. Compounds of this type suitable for use herein are described in EP 1254889. Examples of suitable compounds which contain the residue of an alpha-hydroxycarboxylic acid include (i) methyl-, ethyl-, propyl-, butyl-, pentyl-, hexyl-, benzyl-, phenyl-, and allyl esters of 2-hydroxyisobutyric acid; (ii) methyl-, ethyl-, propyl-, butyl-, pentyl-, hexyl-, benzyl-, phenyl-, and allyl esters of 2-hydroxy-2-methylbutyric acid; (iii) methyl-, ethyl-, propyl-, butyl-, pentyl-, hexyl-, benzyl-, phenyl-, and allyl esters of 2-hydroxy-2-ethylbutyric acid; (iv) methyl-, ethyl-, propyl-, butyl-, pentyl-, hexyl-, benzyl-, phenyl-, and allyl esters of lactic acid; and (v) methyl-, ethyl-, propyl-, butyl-, pentyl-, hexyl-, allyl-, benzyl-, and phenyl esters of glycolic acid. In some embodiments the quaternizing agent comprises methyl 2-hydroxyisobutyrate.

In some embodiments the quaternizing agent comprises an ester of a polycarboxylic acid. In this definition we mean to include dicarboxylic acids and carboxylic acids having more than 2 acidic moieties. In some embodiments the esters are alkyl esters with alkyl groups that contain from 1 to 4 carbon atoms. Suitable example include diesters of oxalic acid, diesters of phthalic acid, diesters of maleic acid, diesters of malonic acid or diesters or triesters of citric acid.

In some embodiments the quaternizing agent is an ester of a carboxylic acid having a pKa of less than 3.5. In such embodiments the compound includes more than one acid group, we mean to refer to the first dissociation constant. The quaternizing agent may be selected from an ester of a carboxylic acid selected from one or more of oxalic acid, phthalic acid, salicylic acid, maleic acid, malonic acid, citric acid, nitrobenzoic acid, aminobenzoic acid and 2,4,6-trihydroxybenzoic acid. In some embodiments the quaternizing agent includes dimethyl oxalate, methyl 2-nitrobenzoate and methyl salicylate.

Any of the quaternizing agents described above, including the hydrocarbyl epoxides, may be used in combination with an acid. Suitable acids include carboxylic acids, such as acetic acid, propionic acid, 2-ethylhexanoic acid, and the like. In some embodiments, for example when the hydrocarbyl acylating agent is a dicarboxylic acylating agent, no separate acid component is needed. In such embodiments, the detergent may be prepared by combining reactants which are essentially free to free of an acid component, such as acetic acid, and rely on the acid group of the hydrocarbyl acylating agent instead.

In some embodiments the quaternary ammonium salt includes the reaction product of: (i) a compound comprising at least one tertiary amino group; and (ii) a quaternizing agent suitable for converting the tertiary amino group of compound (i) to a quaternary nitrogen, where component (i), the compound comprising at least one tertiary amino group, comprises: (a) the condensation product of a hydrocarbyl-substituted acylating agent and a compound having an oxygen or nitrogen atom capable of condensing the acylating agent wherein the condensation product has at least one tertiary amino group.

In some embodiments the hydrocarbyl-substituted acylating agent may be polyisobutylene succinic anhydride and the compound having an oxygen or nitrogen atom capable of condensing with said acylating agent may be dimethylaminopropylamine, dimethyl ethanolamine, diethyl ethanolamine, N-methyl-1,3-diaminopropane, N,N-dimethylaminopropylamine, N,N-diethyl-aminopropylamine, N,N-dimethyl-aminoethylamine, diethylenetriamine, dipropylenetriamine, dibutylenetriamine, triethylenetetraamine, tetraethylenepentaamine, pentaethylenehexaamine, hexamethylenetetramine, and bis(hexamethylene)triamine.

In some embodiments the quaternary ammonium salt comprises an cation represented by the following formula:

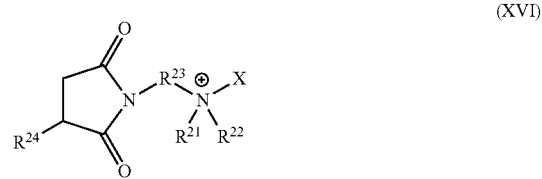 (XVI)

wherein: $R^{21}$ is a hydrocarbyl group containing from 1 to 3 carbon atoms; $R^{22}$ is a hydrocarbyl group containing from 1 to 3 carbon atoms; $R^{23}$ is a hydrocarbylene group containing from 1 to 3 carbon atoms; $R^{24}$ is a hydrocarbyl group containing from 7 to 36 carbon atoms; and X is a group derived from the quaternizing agent.

In some embodiments the quaternary ammonium salt includes the reaction product of: (i) a compound comprising at least one tertiary amino group; and (ii) a quaternizing agent suitable for converting the tertiary amino group of compound (i) to a quaternary nitrogen, where component (i), the compound comprising at least one tertiary amino group, comprises: (b) a polyalkene-substituted amine having at least one tertiary amino group.

In some embodiments the polyalkene substituent of the polyalkene-substituted amine is derived from polyisobutylene and the polyalkene-substituted amine has a number average molecular weight of about 100 to about 500.

In some embodiments the quaternary ammonium salt includes the reaction product of: (i) a compound comprising at least one tertiary amino group; and (ii) a quaternizing agent suitable for converting the tertiary amino group of compound (i) to a quaternary nitrogen, where component (i), the compound comprising at least one tertiary amino group, comprises: (c) a Mannich reaction product having at least one tertiary amino group, wherein the Mannich reaction product is derived from a hydrocarbyl-substituted phenol, an aldehyde, and an amine.

In some embodiments component (i), the compound comprising at least one tertiary amino group, comprises a Mannich reaction product having a tertiary amino group, said Mannich reaction product being prepared from the reaction of a hydrocarbyl-substituted phenol, an aldehyde, and an amine; and wherein the hydrocarbyl substituent of the hydrocarbyl-substituted phenol of component (a) is derived from a polyolefin having a number average molecular weight of 100 to about 400; wherein the aldehyde of component (a) is a formaldehyde or a reactive equivalent thereof; and wherein the amine of component (a) is selected from the group consisting of dimethylamine, ethylenediamine, dimethylaminopropylamine, diethylenetriamine, dibutylamine, and mixtures thereof.

In any of these embodiments described above, any of one or combination of quaternizing agents described above may be used.

INDUSTRIAL APPLICATION

In one embodiment the invention is useful as a liquid fuel for an internal combustion engine. The internal combustion engine includes spark ignition and compression ignition engines; 2-stroke or 4-stroke cycles; liquid fuel supplied via direct injection, indirect injection, port injection and carburetor; common rail and unit injector systems; light (e.g. passenger car) and heavy duty (e.g. commercial truck) engines; and engines fuelled with hydrocarbon and non-hydrocarbon fuels and mixtures thereof. The engines may be part of integrated emissions systems incorporating such elements as; EGR systems; after-treatment including three-way catalyst, oxidation catalyst, NOx absorbers and catalysts, catalyzed and non-catalyzed particulate traps optionally employing fuel-borne catalyst; variable valve timing; and injection timing and rate shaping.

In one embodiment, the composition can comprise more than 3 wt % of a quaternary ammonium salt. In other embodiment, the composition can comprise more than 4, or 5 wt %, or even 10 or 25 wt % of the quaternary ammonium salt.

In another embodiment, the composition can additionally comprise a higher molecular weight quaternary ammonium salt. The higher molecular weight quaternary ammonium salt can comprise (a) a compound comprising (i) at least one tertiary amino group as described above, and (ii) a hydrocarbyl-substituent having a number average molecular weight of from about 500 to about 5000, or up to 2500, or up to 1500; and (b) a quaternizing agent suitable for converting the tertiary amino group of (a)(i) to a quaternary nitrogen, as described above. The higher molecular weight quaternary ammonium salts are more thoroughly described in U.S. Pat. No. 7,951,211, issued May 31, 2011, and U.S. Pat. No. 8,083,814, issued Dec. 27, 2011, and U.S. Publication Nos. 2008/0113890, published May 15, 2008, and 2011/0219674, published Sep. 15, 2011.

In certain embodiments, a composition comprising the quaternary ammonium salt can be employed in a diesel fuel. In a particular embodiment, the diesel fuel can be an ultra-low sulfur diesel fuel, meaning a diesel fuel having less than 30 ppm, or less than 20 ppm, or even less than 15 ppm sulfur.

In an embodiment, a diesel fuel can contain the quaternary ammonium salt composition at from about 10 to about 500 ppm. In another embodiment, the quaternary ammonium salt composition can be present in a diesel fuel at from about 20 to about 250 ppm, or from about 30 to about 120 ppm.

The quaternary ammonium salt composition can be employed in a method of minimizing creation of internal diesel injector deposits. The quaternary ammonium salt can also be employed to reduce the level of pre-existing internal diesel injector deposits. In one embodiment, the quaternary ammonium salt composition can be employed in a method of minimizing creation of internal diesel injector deposits while additionally reducing the level of pre-existing internal diesel injector deposits. Any of the foregoing methods can comprise the steps of supplying to a diesel engine a diesel fuel composition comprising (A) diesel fuel; and (B) a composition of a quaternary ammonium salt as described herein. In one embodiment, the method can include adding the diesel fuel and composition to a diesel engine comprising high pressure common rail diesel injectors.

As used herein, the term "hydrocarbyl substituent" or "hydrocarbyl group" is used in its ordinary sense, which is well-known to those skilled in the art. Specifically, it refers to a group having a carbon atom directly attached to the remainder of the molecule and having predominantly hydrocarbon character. Examples of hydrocarbyl groups include: hydrocarbon substituents, that is, aliphatic (e.g., alkyl or alkenyl), alicyclic (e.g., cycloalkyl, cycloalkenyl) substituents, and aromatic-, aliphatic-, and alicyclic-substituted aromatic substituents, as well as cyclic substituents wherein the ring is completed through another portion of the molecule (e.g., two substituents together form a ring); substituted hydrocarbon substituents, that is, substituents containing non-hydrocarbon groups which, in the context of this invention, do not alter the predominantly hydrocarbon nature of the substituent (e.g., halo (especially chloro and fluoro), hydroxy, alkoxy, mercapto, alkylmercapto, nitro, nitroso, and sulfoxy); hetero substituents, that is, substituents which, while having a predominantly hydrocarbon character, in the context of this invention, contain other than carbon in a ring or chain otherwise composed of carbon atoms. Heteroatoms include sulfur, oxygen, nitrogen, and encompass substituents as pyridyl, furyl, thienyl and imidazolyl. In general, no more than two, preferably no more than one, non-hydrocarbon substituent will be present for every ten carbon atoms in the hydrocarbyl group; typically, there will be no non-hydrocarbon substituents in the hydrocarbyl group.

It is known that some of the materials described above may interact in the final formulation, so that the components of the final formulation may be different from those that are initially added. For instance, metal ions (of, e.g., a detergent) can migrate to other acidic or anionic sites of other molecules. The products formed thereby, including the products formed upon employing the composition of the present invention in its intended use, may not be susceptible of easy description. Nevertheless, all such modifications and reaction products are included within the scope of the present invention; the present invention encompasses the composition prepared by admixing the components described above.

EXAMPLES

The invention will be further illustrated by the following examples, which sets forth particularly advantageous embodiments. While the examples are provided to illustrate the present invention, they are not intended to limit it.

Comparative Sample A:

Comparative Sample A is prepared from a mixture of succinic anhydride prepared from 210 Mn polyisobutylene (350 grams) which is heated with stirring to 105° C. under a nitrogen atmosphere. Tetraethylpentamine (TEPA, 293.9 grams) is added slowly over approximately an hour, maintaining a batch temperature below 120° C. The reaction temperature is increased to 175° C. and held for a further 4.5 hours. The resulting compound is a TEPA succinimide.

Preparatory Sample 1

Preparatory Sample 1 is prepared from a mixture of succinic anhydride prepared from 210 Mn polyisobutylene (800 grams) which is heated with stirring to 105° C. under a nitrogen atmosphere. Dimethylaminopropylamine (DMAPA, 289.9 grams) is added slowly over 95 minutes maintaining batch temperature below 120° C. The reaction temperature is increased to 150° C. and held for a further 3 hours. The resulting compound is a DMAPA succinimide. 1109 grams of the resulting DMAPA succinimide is heated with propylene oxide (257.8 grams), acetic acid (177.75 grams) and 2-ethylhexanol (1156.5 grams) with stirring to reflux (~80° C.) under a nitrogen atmosphere. The resulting compound is a propylene oxide quaternary ammonium salt.

Preparatory Sample 2

Preparatory Sample 2 is prepared from a mixture of 12-hydroxystearic acid (550.2 grams) which is heated with stirring to 100° C. under a nitrogen atmosphere. Dimethylaminopropylamine (DMAPA, 205.5 grams) is added slowly over 23 minutes and held at 100° C. for 3.5 hours, and then heated to 110° C. and held for 17 hours, followed by a final heating to 120° C. and held for 6.5 hours. The resulting compound is a fatty amide. The resultant fatty amide (534.6 grams), propylene oxide (149.57 grams), acetic acid (77.6 grams) and water (5.35 grams) are heated with stirring to reflux (~80° C.) under a nitrogen atmosphere. The resulting compound is a propylene oxide quaternary ammonium salt.

Examples 1 to 5

Fouling Test

The detergents are evaluated in a Direct Injection Fouling Test. The test is described as follows. An ultra-low sulfur diesel (<15 ppm S) plus the respective detergent* is filled into a John Deere 6068 Tier III Powertech 6.8 L 250 hp engine. The torque at test start is consistently between 804 and 850 Nm. The engine is run at 95% load, or 95% of the power capacity the engine can handle maintaining the engine at 1400 rpm before shutting itself down. The engine is maintained at 95% load, as measured by computer, for eight hours of runtime testing and then is shut down and allowed to soak for four hours. During operation, if the % load reaches the 98-99% range, the torque is adjusted downward until the % load comes back to 95%. The reverse process is employed when the load reaches the 92-93% range. Torque measurements are taken every six minutes along with exhaust temperature for each cylinder. After the test, the injectors are disassembled and evaluated for cleanliness. In evaluating effectiveness of the additives, all three of power loss, exhaust temperature change and injector sticking are considered. Minimal power loss, temperature change and no injector sticking are desired. The results of the test are summarized in Table 1.

*Note: In Examples 1, 2 and 4 the active chemical is accompanied by a tall oil fatty acid (TOFA) in the specified ratio of active chemical to TOFA.

TABLE 1

Results in the Fouling Test

| Example | Dose (ppm) | Torque loss (%) | Avg. Exhaust delta (C.) | Internal Injector Deposits? |
|---|---|---|---|---|
| 1 Comparative Sample A + TOFA: 50/50 | 200 | 8.16% | 10.1% | Yes |
| 2 Comparative Sample A + TOFA: 50/50 | 100 | 6.15% | 9.5% | Yes |
| 3 Comparative Sample A | 50 | could not finish test | 8.5% | Yes |
| 4 Preparatory Sample 1 + TOFA: 50/50 | 200 | 0.04% | 2.7% | No |
| 5 Preparatory Sample 2 | 50 | 2.36% | 2.0% | No |

The results of the test show that Comparative Sample A performs poorly in the fouling test and that TOFA acts as a neutral dispersant. In contrast, formulations using quaternary ammonium salt detergents of the present invention do not foul.

Example 6

Clean-Up Test

Given that Sample 1 has been shown not to foul, Sample 1 is tested for clean-up in a Direct Injection Clean-Up Test. The test is described as follows. A mixture of an ultra-low sulfur diesel fuel and a fouling agent is filled into a John Deere 6068 Tier III Powertech 6.8 L 250 hp engine. The engine is run at 1400 rev/minute and 95% load. The engine is maintained at these operating conditions for eight hours of runtime testing and then is shut down and allowed to soak for four hours. During operation, if the % load reaches the 98-99% range, the torque is adjusted downward until the % load comes back to 95%. The reverse process is employed when the load reaches the 92-93% range. After 32 hours of runtime testing, the additive Preparatory Sample 1 is mixed with the fuel mixture being injected into the engine. Further cycles are performed until 49 hours of runtime testing is completed. Torque measurements are taken every six minutes along with the exhaust temperature of each cylinder.

The change in exhaust temperature from 0 to 32 hours, 32 to 49 hours, and over the entire test are summarized in Table 2, and the change in torque from 0 to 32 hours, 32 to 49 hours, and over the entire test are summarized in Table 3.

TABLE 2

Exhaust Temperature Results in the Clean-Up Test

| Exhaust | Exhaust delta (C.) 0-32 hours | Exhaust delta (C.) 32-49 hours | Exhaust delta (C.) overall |
|---|---|---|---|
| 1 | −3.95% | 2.14% | 1.51% |
| 2 | −2.03% | 1.53% | 2.23% |
| 3 | −6.21% | 3.76% | 0.77% |
| 4 | −3.01% | 2.01% | 0.60% |
| 5 | −3.96% | 3.55% | 0.50% |
| 6 | −1.81% | 2.53% | 1.43% |

TABLE 3

Torque and Injector Results in the Clean-Up Test
Torque Change (%)

| 0-32 hours | 32-49 hours | overall |
|---|---|---|
| −10.82% | 7.33% | −0.29% |

The results of the test show that quaternary ammonium salt detergents of the present invention can actually clean injectors.

Each of the documents referred to above is incorporated herein by reference. Except in the Examples, or where otherwise explicitly indicated, all numerical quantities in this description specifying amounts of materials, reaction conditions, molecular weights, number of carbon atoms, and the like, are to be understood as modified by the word "about." Except where otherwise indicated, all numerical quantities in the description specifying amounts or ratios of materials are on a weight basis. Unless otherwise indicated, each chemical or composition referred to herein should be interpreted as being a commercial grade material which may contain the isomers, by-products, derivatives, and other such materials which are normally understood to be present in the commercial grade. However, the amount of each chemical component is presented exclusive of any solvent or diluent oil, which may be customarily present in the commercial material, unless otherwise indicated. It is to be understood that the upper and lower amount, range, and ratio limits set forth herein may be independently combined. Similarly, the ranges and amounts for each element of the invention can be used together with ranges or amounts for any of the other elements. As used herein, the expression "consisting essentially of" permits the inclusion of substances that do not materially affect the basic and novel characteristics of the composition under consideration.

What is claimed is:

1. A composition comprising a quaternary ammonium salt, wherein the quaternary ammonium salt comprises the reaction product of:
   a) a compound comprising
      (i) at least one tertiary amino group, and
      (ii) a hydrocarbyl-substituent derived from a hydrocarbon having a number average molecular weight of from about 100 to about 500;
   b) a quaternizing agent suitable for converting the tertiary amino group of compound (a) to a quaternary nitrogen, said quaternizing agent comprising at least one of dialkyl sulfates; hydrocarbyl substituted carbonates; hydrocarbyl epoxides; or any combination thereof; and
   wherein said quaternary ammonium salt has a cation represented by the following formula:

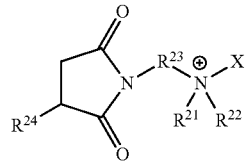

wherein: $R^{21}$ is a hydrocarbyl group containing from 1 to 3 carbon atoms; $R^{22}$ is a hydrocarbyl group containing from 1 to 3 carbon atoms; $R^{23}$ is a hydrocarbylene group containing from 1 to 3 carbon atoms; $R^{24}$ is a hydrocarbyl group containing from 7 to about 36 carbon atoms; and X is a group derived from the quaternizing agent.

2. The composition of claim 1 wherein component a), the compound comprising at least one tertiary amino group and at least one hydrocarbyl-substituent, comprises:
   (I) the condensation product of an acylating agent substituted with the hydrocarbyl-substituent of a)ii) and a compound having an oxygen or nitrogen atom capable of condensing the acylating agent wherein the condensation product has at least one tertiary amino group;
   (II) an amine substituted with the hydrocarbyl-substituent of a)ii), wherein the amine has at least one tertiary amino group and the hydrocarbyl-substituent is a polyalkene-substituent;
   (III) a compound containing at least one hydrocarbyl-substituent of a)ii) and at least one tertiary amino group, wherein the hydrocarbyl-substituent is a polyester group; or
   (IV) any combination thereof.

3. The composition of claim 1 wherein component a), the compound comprising at least one tertiary amino group, comprises the condensation product of a hydrocarbyl-substituted acylating agent and a compound having an oxygen or nitrogen atom capable of condensing with said acylating agent and further having at least one tertiary amino group; and
   wherein the hydrocarbyl-substituted acylating agent is polyisobutylene succinic anhydride and the compound having an oxygen or nitrogen atom capable of condensing with said acylating agent is dimethyl ethanolamine, diethyl ethanolamine, N,N-dimethyl-aminopropylamine, N,N-diethyl-aminopropylamine, N,N-dimethyl-aminoethylamine, and N,N-diethyl-aminoethylamine.

4. The composition of claim 1 wherein component a), the compound comprising at least one tertiary amino group, comprises a polyalkene-substituted amine having at least one tertiary amino group;
   wherein the polyalkene substituent of the polyalkene-substituted amine is derived from polyisobutylene having a number average molecular weight of about 150 to about 500.

5. The composition of claim 1 wherein component b), the quaternizing agent suitable for converting the tertiary amino group of compound a) to a quaternary nitrogen, comprises hydrocarbyl epoxides used in combination with an acid.

6. The composition of claim 1, additionally comprising a second quaternary ammonium salt, wherein the second quaternary ammonium salt comprises the reaction product of:
   a) a compound comprising
      (i) at least one tertiary amino group, and
      (ii) a hydrocarbyl-substituent derived from a hydrocarbon having a number average molecular weight of from about 500 to about 5000;
   b) a quaternizing agent suitable for converting the tertiary amino group of compound (a) to a quaternary nitrogen.

7. A diesel fuel comprising the composition of claim 1.

8. The diesel fuel of claim 7, wherein the diesel fuel is ultra-low sulfur diesel fuel.

9. The diesel fuel of claim 7, wherein the quaternary ammonium salt is present from about 10 to about 500 ppm.

10. A method of minimizing creation of internal diesel injector deposits while additionally reducing the level of pre-existing internal diesel injector deposits comprising the step of supplying to a diesel engine a diesel fuel composition comprising (A) diesel fuel; and (B) a composition according to claim 1.

11. The method of claim 10 wherein the diesel engine comprises high pressure common rail diesel injectors.

* * * * *